US00PP35841P3

(12) United States Plant Patent
Glawe et al.

(10) Patent No.: US PP35,841 P3
(45) Date of Patent: May 28, 2024

(54) ***PELARGONIUM* PLANT NAMED 'KLEPZ22620'**

(50) Latin Name: ***Pelargonium zonale* (L.) L'Hér. ex Aiton**
Varietal Denomination: KLEPZ22620

(71) Applicant: KLEMM + SOHN GMBH & CO. KG, Stuttgart (DE)

(72) Inventors: Martin Glawe, Stuttgart (DE); Nina Neu, Weissach im Tal (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/312,195

(22) Filed: May 4, 2023

(65) Prior Publication Data

US 2023/0371412 P1 Nov. 16, 2023

(30) Foreign Application Priority Data

May 16, 2022 (CH) ..... PBR 22-3522

(51) Int. Cl.
*A01H 5/02* (2018.01)
*A01H 6/42* (2018.01)

(52) U.S. Cl.
USPC ..... Plt./330
CPC ..... *A01H 6/425* (2018.05)

(58) Field of Classification Search
USPC ..... Plt./324, 330
See application file for complete search history.

*Primary Examiner* — Susan McCormick Ewoldt
*Assistant Examiner* — Zachariah Allan Kay
(74) *Attorney, Agent, or Firm* — Weatherly IP Solutions, LLC; James M. Weatherly

(57) ABSTRACT

A new *Pelargonium* plant particularly distinguished by dark green leaves, with a small leaf size and a medium-strong leaf zone, and a red flower color, is disclosed.

1 Drawing Sheet

Genus and species: *Pelargonium zonale* (L.) L'Her. ex Aiton.
Variety denomination: 'KLEPZ22620'.

CROSS-REFERENCE TO RELATED APPLICATION

This patent application claims the benefit of priority from Switzerland Plant Breeders Rights Application No. 22-3522 as filed on May 16, 2022, the contents of which is incorporated herein by reference for all it teaches and discloses.

BACKGROUND OF THE NEW PLANT

The present invention comprises a new and distinct variety of *Pelargonium*, botanically known as *Pelargonium zonale* (L.) L'Her. ex Aiton and hereinafter referred to by the variety name 'KLEPZ22620'. 'KLEPZ22620' originated from a controlled cross in August 2016 in Nairobi, Kenya between the female *Pelargonium* variety 'KLEPZ05141' (U.S. Plant Pat. No. 18,628) and the male *Pelargonium* variety 'KLEPZ17484' (U.S. Plant Pat. No. 30,335).

Seeds from the controlled cross were obtained. The seeds were sown and plants were grown for evaluation. A single plant was selected in June 2017 and subsequently named 'KLEPZ22620'. In July 2017 'KLEPZ22620' was first vegetatively propagated by vegetative stem cuttings in Stuttgart, Germany. 'KLEPZ22620' was found to reproduce true to type in successive generations of asexual propagation via stem cuttings in Stuttgart, Germany.

SUMMARY

The following are the most outstanding and distinguishing characteristics of this new variety when grown under normal horticultural practices in Latina, Italy.

1. Dark green leaves;
2. Small leaf size;
3. A medium to strong leaf zone; and
4. Red flower color,

DESCRIPTION OF THE PHOTOGRAPH

This new *Pelargonium* plant is illustrated by the accompanying photograph which shows an overall view of the plant in a pot. The photograph is of an approximately 14-week-old plant grown indoors in Stuttgart, Germany, in April 2021. The colors shown are as true as can be reasonably obtained by conventional photographic procedures.

DESCRIPTION OF THE NEW VARIETY

The following detailed descriptions set forth the distinctive characteristics of 'KLEPZ22620'. Data was collected on 19-week-old plants in Latina, Italy under greenhouse conditions in April 2023. Color references are to The R.H.S. Colour Chart of The Royal Horticultural Society of London (R.H.S.), 5$^{th}$ edition (2007).

Classification:
*Family*.—Geraniaceae.
*Botanical*.—*Pelargonium zonale* (L.) L'Her. ex Aiton.
*Common*.—*Pelargonium*.
*Designation*.—'KLEPZ22620'.

Parentage:
*Female parent*.—'KLEPZ05141' (U.S. Plant Pat. No. 18,628).
*Male parent*.—'KLEPZ17484' (U.S. Plant Pat. No. 30,335).

Plant:
*Form*.—Bushy.
*Habit*.—Upright.
*Height* (*from top of soil*).—20.0 cm.
*Width* (*horizontal plant diameter*).—29.0 cm.
*Natural flowering season*.—March to October.
*Propagation type*.—Vegetative by stem cuttings.
*Time to produce a finished flowering plant*.—12 weeks.
*Time to initiate and develop roots*.—4 weeks.
*Root description*.—Fine, dense, white (RHS N155B).

Stems:
*Quantity of stems per plant*.—5 to 7.
*Color*.—RHS 146B.
*Surface texture*.—Pubescent.
*Stem form*.—Round.
*Diameter*.—0.8 cm.
*Length*.—15 to 20 cm.
*Internode length*.—1.3 cm to 1.5 cm.
*Anthocyanin*.—Present, color is RHS 165A.

Leaves:
*Arrangement*.—Alternate.
*Shape*.—Reniform.
*Apex*.—Round.
*Base*.—Open.
*Margin*.—Crenate.
*Surface texture both surfaces*.—Pubescent.
*Length*.—5.4 cm.
*Width*.—6.6 cm.
*Color*.—Upper surface: RHS 147A. Lower surface: RHS 147B.
*Zonation*.—Strong, located in the middle of leaf, with a width of 1.5 cm.
*Zonation color*.—RHS 202A.
*Depth of sinus*.—1.2 cm.
*Petiole*.—Length: 4.0 cm. Diameter: 0.3 cm. Color: RHS 146B. Strength: Medium.
*Venation pattern*.—Palmate.
*Venation color*.—Upper surface: RHS 147A. Lower surface: RHS 146B.

Inflorescence:
*Lastingness of flowers on the plant*.—6 to 8 days.
*Umbels*.—Quantity of umbels per plant: 5 to 6. Length: 6.6 cm. Diameter: 12.0 cm.
*Individual florets of the umbel*.—Quantity of florets per umbel: 13 to 19. Depth: 2.0 cm. Diameter: 5.3 cm.
*Fragrance*.—Absent.

Flower buds:
*Cluster shape*.—Round.
*Cluster size*.—Length: 1.4 cm. Width: 2.0 cm.
*Surface texture*.—Pubescent.
*Bud*.—Height: 0.7 cm to 1.2 cm. Width: 0.5 cm to 1.0 cm. Shape: Round. Apex: Acute. Base: Obtuse. Margin: Entire. Color: RHS 146B.

Petals:
*Quantity per flower*.—8.
*Shape*.—Spatulate.
*Apex*.—Round.
*Base*.—Obtuse.
*Margin*.—Entire.
*Length*.—2.2 cm.
*Width*.—2.1 cm.
*Surface texture*.—Upper surface: Smooth. Lower surface: Smooth.
*Color of lobes*.—Upper lobes: Upper surface: RHS 42A. Lower surface: RHS 43B. Lower lobes: Upper surface: RHS 42A. Lower surface: RHS 43B.

Petaloids:
*Quantity per flower*.—3 to 5.
*Shape*.—Crippled, different shapes from drepanium to linear to flame like.
*Apex*.—Acute and round.
*Base*.—Obtuse.
*Margin*.—Entire.
*Length*.—0.5 cm to 1.2 cm.
*Width*.—0.2 cm to 0.6 cm.
*Surface texture*.—Upper surface: Smooth. Lower surface: Smooth.
*Color*.—Upper surface: RHS 42A. Lower surface: RHS 43B.

Sepals:
*Number per flower*.—5.
*Shape*.—Elliptic.
*Apex*.—Acute.
*Base*.—Obtuse.
*Margin*.—Entire.
*Surface texture*.—Upper surface: Smooth. Lower surface: Pubescent.
*Color*.—Upper surface: RHS 146C, RHS 178A at the base. Lower surface: RHS 146C, RHS 178A at the base.
*Length*.—1.5 cm.
*Width*.—0.4 cm.

Pedicel:
*Length*.—3.8 cm.
*Diameter*.—0.2 cm.
*Color*.—RHS 178B.
*Surface texture*.—Pubescent.
*Strength*.—Medium.

Peduncle:
*Length*.—10.2 cm.
*Diameter*.—0.4 cm.
*Color*.—RHS 146A.
*Texture*.—Pubescent.
*Strength*.—Strong.

Reproductive organs:
*Stamens*.—Quantity per flower: 3 to 5. Anther length: 0.2 cm. Filament length: 0.8 cm. Filament color: RHS 69C. Pollen amount: Medium. Pollen color: RHS N25A.
*Pistils*.—Number: 1. Stigma color: RHS 45A. Style length: 0.4 cm. Style color: RHS 45A. Ovary arrangement: Central. Ovary color: RHS 174A. Ovary diameter: 0.2 cm. Ovary length: 0.6 cm. Ovary Texture: Pubescent.

Fruit and seed set: None observed.

Disease and pest/insect resistance: None observed.

COMPARISON WITH PARENTAL LINES AND KNOWN VARIETY

'KLEPZ22620' is distinguished from its parents as described in Table 1.

TABLE 1

| Comparison with Parental Lines | | | |
|---|---|---|---|
| Characteristic | 'KLEPZ22620' | Female parent | Male parent |
| Leaf color | Dark green leaves | Green leaves | Dark green leaves |
| Leaf size | Small | Medium to big | Medium |
| Flower Color | Red | Orange red | Purple red |

'KLEPZ22620' can be compared to the commercial variety 'KLEPZ15357' (U.S. Plant Pat. No. 28,712). Differences between the two varieties are described in Table 2:

TABLE 2

| Comparison with Similar Variety | | |
|---|---|---|
| Characteristic | 'KLEPZ22620' | 'KLEPZ15357' |
| Leaf zone | Medium to strong | Very weak |
| Flower Color | Red | Orange red |

We claim:

1. A new and distinct variety of *Pelargonium* plant named 'KLEPZ22620' as illustrated and described herein.

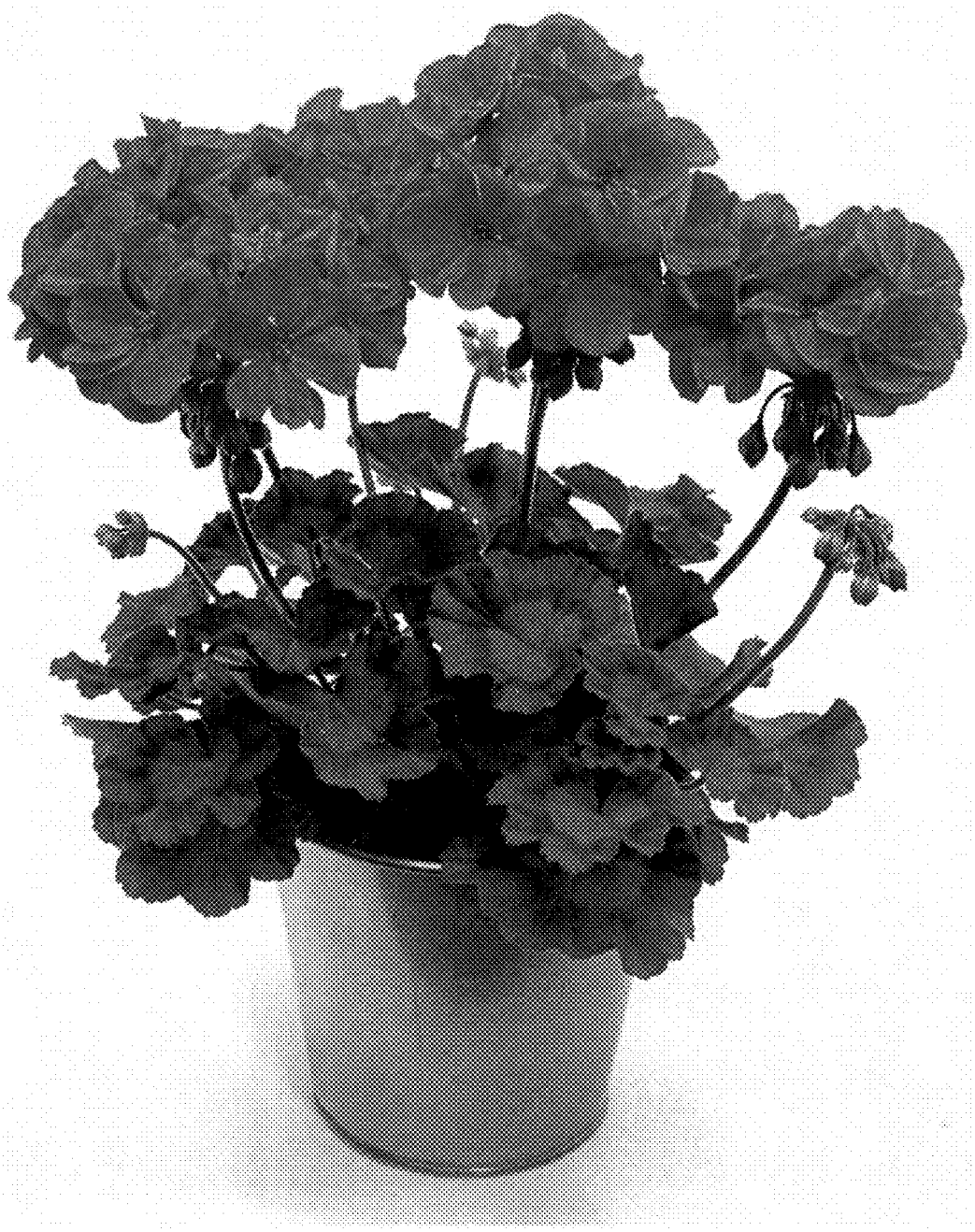

* * * * *